United States Patent [19]

Weissmüller et al.

[11] Patent Number: 4,804,659
[45] Date of Patent: Feb. 14, 1989

[54] DECAHYDRONAPHTH-2-YL-ALKYLA-MINES

[75] Inventors: Joachim Weissmüller, Monheim; Paul Reinecke, Leverkusen, both of Fed. Rep. of Germany

[73] Assignee: Bayer Aktiengesellschaft, Leverkusen, Fed. Rep. of Germany

[21] Appl. No.: 70,854

[22] Filed: Jul. 8, 1987

[30] Foreign Application Priority Data

Jul. 22, 1986 [DE] Fed. Rep. of Germany ....... 3624648

[51] Int. Cl.⁴ ............................................ C07D 265/30
[52] U.S. Cl. ................................. 514/237.8; 564/454; 564/460; 514/255; 514/277; 514/319; 544/106; 544/336; 546/192; 546/195
[58] Field of Search ................. 564/454, 460; 514/659, 514/661, 237.8, 277, 319, 255, 241; 544/106, 336, 180, 63, 65, 66, 224; 546/195, 192

[56] References Cited

U.S. PATENT DOCUMENTS 4,131,744 12/1978 Sandeen et al. .................... 564/454

FOREIGN PATENT DOCUMENTS 0019769 12/1980 European Pat. Off. ............ 564/454
0032673 7/1981 European Pat. Off. ............ 564/454
0161455 11/1985 European Pat. Off. ............ 564/454
3413897 10/1985 Fed. Rep. of Germany ...... 564/454

Primary Examiner—Richard L. Raymond
Assistant Examiner—Raymond Covington
Attorney, Agent, or Firm—Sprung Horn Kramer & Woods

[57] ABSTRACT

Novel fungicidally active decahydronaphth-2-yl-alkylamines of the formula

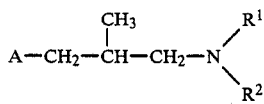

in which A represents optionally substituted decahydronaphth-2-yl and $R^1$ and $R^2$ are identical or different and represent alkyl or alkenyl, or $R^1$ and $R^2$, together with the nitrogen atom to which they are bound, represent an optionally substituted, saturated heterocycle which may contain further hetero atoms, or a plant-tolerated acid-addition salts thereof.

9 Claims, No Drawings

DECAHYDRONAPHTH-2-YL-ALKYLAMINES

The invention relates to new decahydronaphth-2-yl-alkylamines, a process for the preparation thereof, and the use thereof as fungicides.

It is already known that certain β-naphthylalkylamines, such as, for example, cis-1-(2,6-dimethyl-morpholin-4-yl)-2-methyl-3-(6-methyl-naphth-2-yl)-propane, have fungicidal properties (cf. DE-OS (German Published Specification) 3,413,897). However, the action of these compounds is not always completely satisfactory under certain conditions, particularly at low application amounts and concentrations.

New decahydronaphth-2-yl-alkylamines of the general formula (I)

$$A-CH_2-\underset{\underset{CH_3}{|}}{CH}-CH_2-N\diagup^{R^1}_{R^2} \quad (I)$$

in which

A represents optionally substituted decahydronaphth-2-yl and $R^1$ and $R^2$ are identical or different and represent alkyl or alkenyl, or $R^1$ and $R^2$, together with the nitrogen atom to which they are bound, represent an optionally substituted, saturated heterocycle, which may contain further hetero atoms, and also the acid-addition salts thereof which are tolerated by plants, have been found.

It has furthermore been found that the new decahydronaphth-2-yl-alkylamines of the general formula (I)

$$A-CH_2-\underset{\underset{CH_3}{|}}{CH}-CH_2-N\diagup^{R^1}_{R^2} \quad (I)$$

in which

A represents optionally substituted decahydronaphth-2-yl and $R^1$ and $R^2$ are identical or different and represent alkyl or alkenyl, or $R^1$ and $R^2$, together with the nitrogen atom to which they are bound, represent an optionally substituted, saturated heterocycle, which may contain further hetero atoms, and also the acid-addition salts thereof which are tolerated by plants, are obtained when β-naphthylalkylamine compounds of the general formula (II)

$$Ar-CH_2-\underset{\underset{CH_3}{|}}{CH}-CH_2-N\diagup^{R^1}_{R^2} \quad (II)$$

in which

Ar represents optionally substituted β-naphthyl and
$R^1$ and $R^2$ have the abovementioned meaning, are hydrogenated using hydrogen, if appropriate in the presence of a catalyst and if appropriate in the presence of a diluent, if appropriate under pressure, and, if appropriate, an acid-addition reaction is subsequently carried out.

The new decahydronaphth-2-yl-alkylamines of the formula (I) contain chiral centers and are generally obtained in the form of mixtures (racemates or diastereomeric mixtures). The diastereomers can be isolated, if appropriate, in pure form in a generally known fashion, such as, for example by column chromatography or based on solubility differences. Unary enantiomers can be obtained from such diastereomers using known methods. These are covered by the present invention, as are the mixtures thereof.

Finally, it has been found that the new decahydronaphth-2-yl-alkylamines of the formula (I) have good fungicidal properties. Here, the compounds according to the invention surprisingly exhibit a better activity than the β-naphthyl-alkylamines which are known from the state of the art, such as, for example, cis-1-(2,6-dimethylmorpholin-4-yl)-2-methyl-3-(6-methyl-naphth-2-yl)-propane, which are similar compounds chemically and regarding their action.

The decahydronaphth-2-yl-alkylamines according to the invention are generally defined by the formula (I). Preferred compounds of the formula (I) are those in which A represents decahydronaphth-2-yl which is optionally mono- to trisubstituted, identically or differently, where the following may be mentioned as substituents: hydroxyl, in each case straight-chain or branched alkyl and alkoxy in each case having 1 to 6 carbon atoms;

$R^1$ and $R^2$ are identical or different and in each case represent straight-chain or branched alkyl or alkenyl in each case having up to 6 carbon atoms, or $R^1$ and $R^2$, together with the nitrogen atom to which they are bound, represent a saturated five- to seven-membered heterocycle which may contain 1 or 2 further hetero atoms, particularly nitrogen or oxygen, and which is optionally mono- to trisubstituted, identically or differently, suitable substituents being: in each case straight chain or branched alkyl or hydroxyalkyl in each case having 1 to 4 carbon atoms.

Particularly preferred decahydronaphth-2-yl-alkylamines of the formula (I) are those in which A represents decahydronaphth-2-yl which is optionally mono- or disubstituted, identically or differently, where the following may be mentioned as substituents: hydroxyl, methyl, ethyl, n- or i-propyl; n-, i-, s- or t-butyl, methoxy, ethoxy or n- or i-propoxy;

$R^1$ and $R^2$ are identical or different and represent methyl, ethyl, n- or i-propyl or n-, i- or s-butyl; or also represent allyl, butenyl, dimethylallyl or n- or i-pentenyl, or $R^1$ and $R^2$, together with the nitrogen atom to which they are bound, represent a heterocycle of the formula $$-N\diagdown\diagup, \quad -N\diagdown\diagup\diagdown, \quad -N\diagdown\diagup\diagdown_{CH_2}^{CH_2} \text{ or } -N\diagdown\diagup O$$

which is optionally mono- to trisubstituted, identically or differently, suitable substituents being methyl, ethyl or hydroxymethyl.

Very particularly preferred decahydronaphth-2-yl-alkylamines of the formula (I) are those in which A represents decahydronaphth-2-yl which is optionally mono- or disubstituted by methyl, and R¹ and R², together with the nitrogen atom to which they are bound, represent a heterocycle of the formula

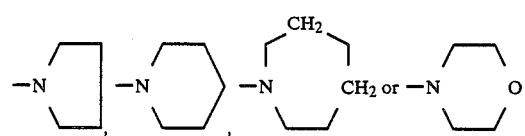

which is optionally mono- to trisubstituted by methyl.

In addition to the compounds mentioned in the preparation examples, the following decahydronaphth-2-yl-alkylamines of the formula (I) may be mentioned individually:

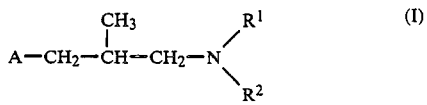

| A | R¹ | R² or —N⟨R¹/R² |
|---|---|---|
| 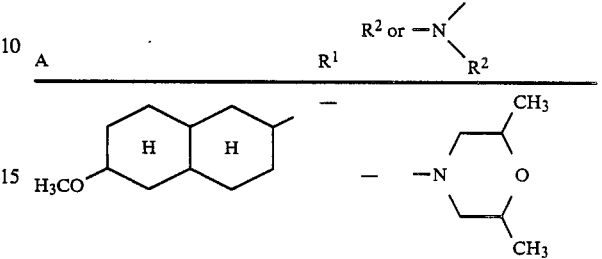 | | |

If, for example, cis-1-(2,6-dimethylmorpholin-4-yl)-2-methyl-3-β-(6-methylnaphthyl)-propane is used as starting material, then the course of the reaction of the process according to the invention may be represented by the following equation:

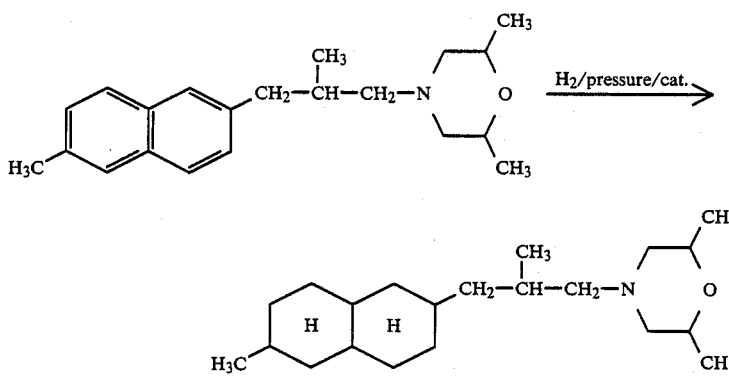

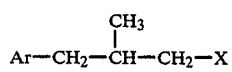

The β-naphthyl-alkylamine compounds which are required as starting materials for carrying out the process according to the invention are generally defined by the formula (II). In this formula, $R^1$ and $R^2$ preferably represent those meanings which have preferably already been mentioned in connection with the description of the substances, according to the invention, of the formula (I) for these substituents. Ar preferably represents β-naphthyl which is optionally mono- to trisubstituted, identically or differently, where the following may preferably be mentioned as substituents: hydroxyl; straight-chain or branched alkyl and alkoxy in each case having 1 to 6 carbon atoms.

The β-naphthylalkylamine compounds of the formula (II) are known (cf. DE-OS (German Published Specification) 3,413,897) or can be obtained by the processes described there, for example by reacting β-naphthyl derivatives of the general formula (III)

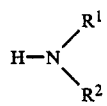

in which
Ar has the abovementioned meaning and
X represents an electron-withdrawing leaving group, such as, for example, methanesulphonyloxy, p-toluenesulphonlyloxy or halogen,
with known amines of the general formula (IV)

$$H-N\begin{matrix}R^1\\R^2\end{matrix}\qquad\text{(IV)}$$

in which
$R^1$ and $R^2$ have the abovementioned meaning, if appropriate in the presence of a diluent, such as, for example, ethers or amides, and if appropriate in the presence of an acid acceptor, such as, for example, tertiary amines, at temperatures between 30° C. and 180° C.

The β-naphthyl derivatives of the formula (III) are known (cf. DE-OS (German Published Specification) 3,413,897) or can be obtained by the processes described there when 2-methyl-3-β-naphthyl-acrylates of the general formula (V)

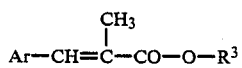

in which
Ar has the abovementioned meaning and $R^3$ represents alkyl, particularly methyl or ethyl, are initially reduced in a first stage using a reducing agent, such as, for example, lithium aluminum hydride, if appropriate in the presence of a diluent, such as, for example, diethyl ether, at temperatures between −20° C. and +60° C., and the alcohols of the general formula (VI),

in which
Ar has the abovementioned meaning, thus obtained are derivatized by generally conventional processes, thus, for example, either sulphonated using sulphonyl halides of the general formula (VII)

in which
$R^4$ represents in each case optionally substituted alkyl or aryl, particularly methyl, trifluoromethyl or p-tolyl, and
Hal represents halogen, particularly chlorine or bromine,
if appropriate in the presence of a diluent, such as, for example, dichloromethane, and if appropriate in the presence of an acid acceptor, such as, for example, triethylamine, at temperatures between −20° C. and +120° C., or halogenated in the presence of a halogenating agent, such as thionyl chloride, phosphorus pentachloride, phosphorus tribromide, hydrobromic acid or hydroiodic acid, if appropriate in the presence of a diluent, such as, for example, tetrachloromethane, and if appropriate in the presence of a catalyst, such as, for example, pyridine, at temperatures between +20° C. and +180° C.

The 2-methyl-3-β-naphthylacrylates of the formula (V) are known (cf., for example, Indian J. Chem. Section 8, 22B (4) 352-354 [1983], J. Org. Chemistry 33, 4351-4362 [1968] or DE-OS (German Published Specification) 3,413,897), or can be prepared in a simple analogous fashion by processes which are known in principle (cf., for example, J. Chem. Soc. 1961, 3160). The sulphonyl halides of the formula (VII) are generally known compounds of organic chemistry.

Suitable diluents for carrying out the process according to the invention are inert organic solvents. These preferably include aliphatic hydrocarbons, such as petroleum ether, hexane or cyclohexane; ethers, such as diethyl ether, dioxane, tetrahydrofuran or ethylene glycol dimethyl or diethyl ether; esters, such as ethyl acetate; sulphoxides, such as dimethyl sulphoxide; and alcohols, such as methanol or ethanol.

Suitable catalysts for carrying out the process according to the invention are conventional hydrogenation catalysts. Noble metal, noble metal oxide or noble metal hydroxide catalysts or so-called Raney catalysts, such as, particularly, platinum, platinum oxide, nickel and ruthenium, are preferably used.

The reaction temperatures may be varied within a relatively wide range when carrying out the process according to the invention. In general, the reaction is carried out at temperatures between 20° C. and 250° C., preferably at temperatures between 20° C. and 200° C.

The process according to the invention may be carried out at atmospheric pressure or alternativly at increased pressure. In general, the process is carried out between 1 atm and 300 atm, preferably at 1 atm and 200 atm.

However, it is also possible to prepare the new decahydronaphth-2-yl-alkylamines of the formula (I) by another process, for example by hydrogenating the alcohols of the formula (VI) analogously to the abovementioned process according to the invention; derivatizing the corresponding decahydronaphth-2-yl derivatives

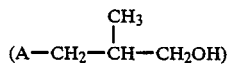

by generally conventional processes, and reacting the compouds

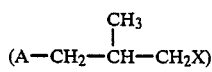

thus obtained with the amines of the formula (IV) according to the abovementioned process, to form the new compounds of the formula (I).

The compounds, according to the invention, of the formula (I) may, if appropriate, subsequently be converted into acid addition salts.

The following acids are preferably suitable for the preparation of physiologically acceptable acid addition salts of the compounds of the formula (I): hydrohalic acids, such as, for example, hydrochloric acid and hydrobromic acid, particularly hydrochloric acid, furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Preferred acid-addition compounds here are the addition compounds with hydrogen chloride, p-toluenesulphonic acid, methanesulphonic acid, 1,6-dinaphthalenesulphonic acid, formic acid and acetic acid.

The acid-addition salts of the compounds of the formula (I) can be obtained in a simple fashion by conventional salt-formation methods, such as, for example, by dissolving a compound of the formula (I) in a suitable inert solvent and adding the acid, such as, for example, hydrochloric acid, and isolated in a known fashion, for example by filtering off, and, if appropriate, purified by washing with an inert organic solvent.

The active compounds according to the invention have a strong microbicidal action and can be used in practice for combating undesired microorganisms. The active compounds are suitable for use as plant-protection agents.

Thus, for example, fungicidal agents are employed in plant protection for combating Plasmodiophoromycetes, Oomycetes, Chytridiomycetes, Zygomycetes, Ascomycetes, Basidomycetes, Deuteromycetes.

Some causative organisms of fungal diseases included under the abovementioned main headings, are mentioned below as non-limiting examples:

Phytophthora species, such as, for example, *Phytophthora infestans;*

Pseudoperonospora species, such as, for example, *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graninis;*

Sphaerotheca species, such as for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea;*

(Conidial form: Drechslera, Synonym; Helminthosporium); Cochliobolus species, such as, for example, *Cochliobolus sativus;*

(Conidial form: Drechslera Synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cerospora canescens;*

Alternaria species, such as, for example, *Alternaria brassicae;*

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention may be used particularly successfully for combating cereal diseases, such as, for example, *Erysiphe graminis*,

*Septoria nodorum* and *Drechslera teres*, furthermore for combating true mildew and Phytophthora, and also *Pyricularia oryzae* on rice. In addition, the substances according to the invention exhibit a good action in the mycelia growth test.

The active compounds can be converted to the customary formulations, such as solutions, emulsions suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated armatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide, N-methylpyrrolidone and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin substances, azo substances and metal phthalocyanine substances, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compound can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

Example 1

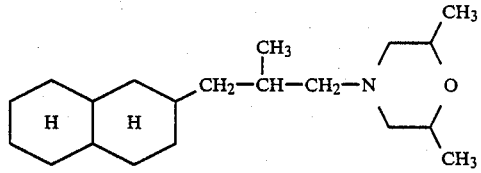

10 g (0.033 mol) of 1-[cis-2,6-dimethylmorpholin-4-yl]-2-methyl-3-β-naphthyl-propane are hydrogenated for 3 hours in 150 ml of tetrahydrofuran at 120° C. in the presence of 3 g of ruthenium on charcoal (5%) and at a hydrogen pressure of 150 bar. The catalyst is filtered off, and the solvent is evaporated in vacuo.

7.7 g (74.6% of theory) of 1-[cis-2,6-dimethylmorpholin-4-yl]-2-methyl-3-[decahydronaphth-2-yl]-propane of refractive index $n_D^{20} = 1.4869$ are obtained.

Preparation of the starting compound

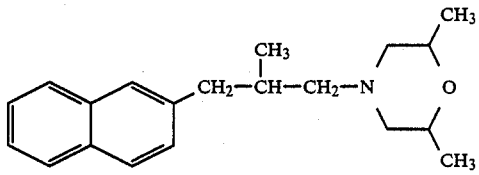

10.8 g (0.04 mol) of 1-methanesulphonyloxy-2-methyl-3-β-naphthyl propane and 9 g (0.078 mol) of cis-2,6-dimethylmorpholine are stirred for 15 hours at a bath temperature of 140° C. Water is added to the resultant reaction mixture, which is extracted repeatedly with ether. The combined organic phases are dried over sodium sulphate and freed from solvent in vacuo; the oily residue is purified by column chromatography (silica gel 60, petroleum ether/ethyl acetate=2:1).

6.2 g (52% of theory) of cis-1-(2,6-dimethylmorpholin-4-yl)-2-methyl-3-β-naphthyl-propane of refractive index $n_D^{20}=1.5527$ are obtained.

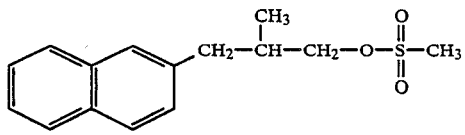

11 g (0.1 mol) of methanesulphonyl chloride are added dropwise, with stirring at 0° C. to 14 g (0.074 mol) of 2-methyl-3-β-naphthylpropanol (crude) in 80 ml of absolute pyridine, the mixture is stirred for a further 16 hours at room temperature after the addition is complete, excess pyridine is removed by distillation in vacuo, the residue is taken up in water, extracted repeatedly with dichloromethane and dried over sodium sulphate, and the solvent is removed in vacuo. 13.6 g (66% of theory) of 1-methanesulphonyloxy-2-methyl-3-β-naphthyl-propane are obtained as an oil. (IR: $\nu=1345$, 1180 cm$^{-1}$).

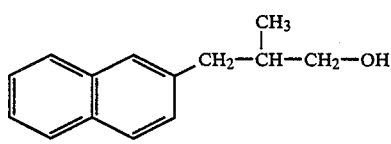

12 g (0.05 mol) of ethyl 2-methyl-3-β-naphthylacrylate are added dropwise, with cooling in ice, under a dry nitrogen atmosphere to a suspension of 1.9 g (0.05 mol) of lithium aluminum hydride in 150 ml of absolute ether. When the addition is complete, the reaction mixture is refluxed for 8 hours and the, after cooling, 15 ml of 5% strength sulphuric acid are slowly added dropwise with cooling, the precipitated solid is filtered off under suction, the filtrate is dried over sodium sulphate, the solvent is removed in vacuo, and the residue is recrystallized from ether/petroleum ether. 7.1 g of 2-methyl-3-β-naphthyl-propanol, of melting point 71°–74° C., which, according to a gas chromatogram, is contaminated with 2-methyl-1-β-naphthyl-propen-3-ol and which is employed in the next reaction stage without further purification, are obtained.

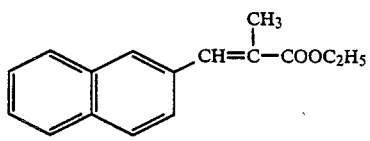

40 g (0.2 mol) of ethyl α-ethoxalylpropionate are added at 70° C. to a suspension of 5.5 g (0.2 mol) of 80% purity sodium hydride in 300 ml of absolute xylene. When the hydrogen evolution is complete, 31.2 g (0.2 mol) of β-naphthaldehyde, dissolved in xylene, are added dropwise and the mixture is boiled for 90 minutes after the addition is complete.

150 ml of water are added to the cooled reaction mixture, and the organic phase is separated off, washed with 7% strength sodium carbonate solution, dried over sodium sulphate and concentrated. The residue is distilled in vacuo. 21.7 g (45.2% of theory) of ethyl 2-methyl-3-β-naphthyl-acrylate of boiling point 110° C. (0.13 mbar) are obtained.

The following compounds of the general formula (I)

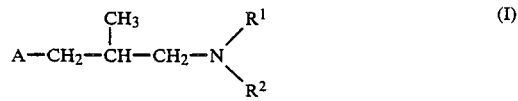

are obtained in an analogous fashion and according to the general process instructions:

| Ex. No. | A | $-N\begin{matrix}R^1\\R^2\end{matrix}$ | Refractive index ($n_D^{20}$) |
|---|---|---|---|
| 2 | H₃C–[decalin]– | $-N\begin{matrix}CH(CH_3)\\CH_2\\O\\CH(CH_3)\end{matrix}$ | 1.4954 |
| 3 | H₃C–[decalin]– | –N(piperidinyl) | 1.4941 |
| 4 | H₃C–[decalin]– | $-N\begin{matrix}CH(CH_3)\\\\CH(CH_3)\end{matrix}$ | 1.4881 |

Use Example

In the following use example, the compound specified below is employed as comparison substance:

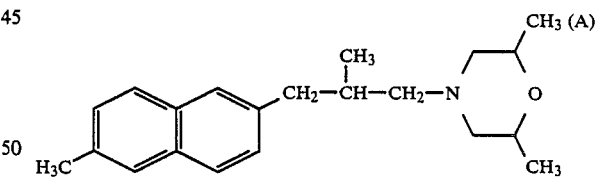

cis-1-(2,6-dimethyl-morpholin-4-yl)-2-methyl-3-(6-methylnaphth-2-yl)-propane.

Example A

Erysiphe test (barley)/protective.
Solvent: 100 parts by weight of dimethylformamide.
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis f.sp. hordei.*

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown by the compounds according to the invention.

It will be appreciated that the instant specification and claims are set forth by way of illustration and not limitation, and that various modifications and changes may be made without departing from the spirit and scope of the present invention.

We claim:

1. A decahydronaphth-2-yl-alkylamine of the formula

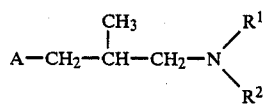

in which
A represents optionally substituted decahydronaphth-2-yl and
$R^1$ and $R^2$ are identical of different and represent alkyl or alkenyl, or
$R^1$ and $R^2$, together with the nitrogen atom to which they are bound, represent a saturated six-membered heterocycle which may contain 1 or 2 further hetero atoms in the form of nitrogen or oxygen and which is optionally mono- to trisubstituted, identically or differently, by in each case straight-chain or branched alkyl or hydroxyalkyl in each case having 1 to 4 carbon atoms
or a plant-tolerated acid-addition salt thereof.

2. A decahydronaphth-2-yl-alkylamine or salt thereof according to claim 1, in which
A represents decahydronaphth-2-yl which is optionally mono- to trisubstituted, identically or differently, by hydroxyl, or by in each case straight-chain or branched alkyl or alkoxy in each case having 1 to 6 carbon atoms,
$R^1$ and $R^2$ are identical or different and represent in each case straight-chain or branched alkyl or alkenyl in each case having up to 6 carbon atoms, or
$R^1$ and $R^2$, together with the nitrogen atom to which they are bound, represent a saturated six-membered heterocycle which may contain 1 or 2 further hetero atoms in the form of nitrogen or oxygen and which is optionally mono- to trisubstituted, identically or differently, by in each case straight-chain or branched alkyl or hydroxyalkyl in each case having 1 to 4 carbon atoms.

3. A decahydronaphth-2-yl-alkylamine or salt thereof according to claim 1, in which
A represents decahydronaphth-2-yl which is optionally mono- or disubstituted, identically or differently, by hydroxyl, methyl, n- or i- propyl; n-, i-, s- or t-butyl, methoxy, ethoxy or n- or i-propoxy,
$R^1$ and $R^2$ are identical or different and represent methyl, ethyl, n- or i-propyl and n-, i- or s-butyl; or also represent allyl, butenyl, dimethylallyl or n- or i-pentenyl, or $R^1$ and $R^2$, together with the nitrogen atom to which they are bound, represent a heterocycle of the formula

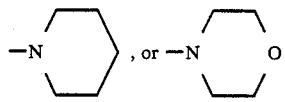

which is optionally mono- to trisubstituted, identically or differently, by methyl, ethyl or hyroxymethyl.

4. A decahydronaphth-2-yl-alkylamine or salt thereof according to claim 1, in which
A represents decahydronaphth-2-yl which is optionally mono- or disubstituted by methyl, and
$R^1$ and $R^2$, together with the nitrogen atom to which they are bound, represent a heterocycle of the formula

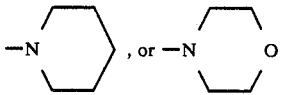

'which is optionally mono- to trisubstituted by methyl.

5. A compound according to claim 1, wherein such compound is 1-(2,6-dimethylmorpholin-4-yl)-2-methyl-3-(decahydronaphth-2-yl)-propane of the formula

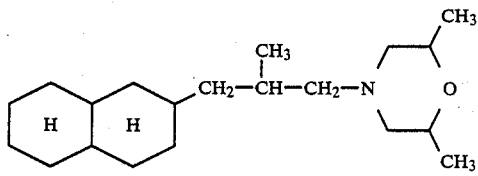

or a plant-tolerated acid-addition salt thereof.

6. A compound according to claim 1, wherein such compound is 1-(2,6-dimethyl-morpholin-4-yl)-2-methyl-3-(6-methyl-decahydronaphth-2-yl)-propane of the formula

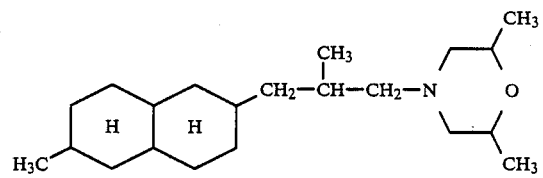

or a plant-tolerated acid-addition salt thereof.

7. A compound according to claim 1, wherein such compound is 1-(piperidin-1-yl)-2-methyl-3-(6-methyl-decahydronaphth-2-yl)-propane of the formula

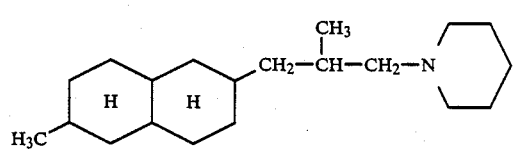

or a plant-tolerated acid-addition salt thereof.

8. A compound according to claim 1, wherein such compound is 1-(3,5-dimethyl-piperidin-1-yl)-2-methyl-3-(6-methyl-decahydronaphth-2-yl)-propane of the formula
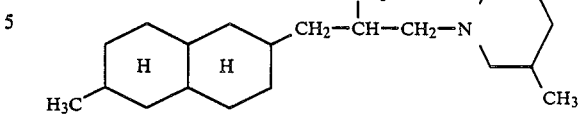
or a plant-tolerated acid-addition salt.
9. A fungicidal composition comprising a fungicidally effective amount of a compound or salt according to claim 1 and a diluent.
* * * * *